US00PP16224P3

(12) United States Plant Patent
Korlipara

(10) Patent No.: US PP16,224 P3
(45) Date of Patent: Jan. 31, 2006

(54) *VERBASCUM* PLANT NAME 'SUGAR PLUM'

(50) Latin Name: *(Verbascum phoeniceum×V. dumulosum)×V. phoeniceum*
Varietal Denomination: Sugar Plum

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 176 days.

(21) Appl. No.: 10/871,830

(22) Filed: Jun. 18, 2004

(65) Prior Publication Data

US 2005/0283874 P1 Dec. 22, 2005

(51) Int. Cl.
*A01H 5/00* (2006.01)

(52) U.S. Cl. ..... Plt./263

(58) Field of Classification Search ..... Plt./263
See application file for complete search history.

(56) References Cited

U.S. PATENT DOCUMENTS

PP14,167 P2 * 9/2003 Rijnbeek ..... Plt./263
PP14,793 P2 * 5/2004 Oudshoorn ..... Plt./263
2002/0194661 P1 * 12/2002 Heims ..... Plt./263

OTHER PUBLICATIONS http://www.terranovanurseries.com/pages/plantsT3.html.*

* cited by examiner

*Primary Examiner*—Kent Bell
*Assistant Examiner*—W. C. Haas
(74) *Attorney, Agent, or Firm*—Klarquist Sparkman, LLP

(57) ABSTRACT

A new and distinct *Verbascum* plant characterized by numerous purple flowers on numerous short, upright flowering stems, a compact habit, and excellent vigor.

1 Drawing Sheet

Botanical classification: (*Verbascum phoeniceum×V. dumulosum*)×*V. phoeniceum.*

Variety denomination: 'Sugar Plum'.

The present invention relates to a new and distinct cultivar of *Verbascum* hybrid given the cultivar name 'Sugar Plum'. *Verbascum* is in the family Scrophulariaceae.

This new cultivar originated from a cross between *Verbascum* 'Jackie' (an unpatented plant) as the seed parent and an unnamed selection of *Verbascum phoeniceum* (an unpatented plant) as the pollen parent. *Verbascum* 'Jackie' is an unpatented plant and a cross between *Verbascum phoeniceum* and *Verbascum dumulosum.*

This new *Verbascum* hybrid is unique in its purple flower color combined with its *Verbascum* 'Jackie'-like compact habit and short, multiple flowering stems.

This patent is characterized by the following:

1. Large purple flowers.
2. Numerous upright flowering stems.
3. Compact habit.
4. Short flowering stems.
2. Excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done by Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The photograph shows the whole plant of *Verbascum* 'Sugar Plum' growing in the trial fields in July in Canby, Oreg.

DETAILED PLANT DESCRIPTION

The following is a detailed description of the new *Verbascum* selection based on observations of one-year-old specimens grown in the ground in full sun under typical outdoor conditions in the trials fields in Canby, Oreg. Canby is Zone 8 on the USDA Hardiness map. Temperatures range from a high of 95 degrees F. in August to 32 degrees F. in January. Normal rainfall in Canby is 42.8 inches per year. The color descriptions are all based on The Royal Horticultural Society Colour Chart.

Botanical classification: (*Verbascum phoeniceum×V. dumulosum*)×*V. phoeniceum.*

Variety denomination: 'Sugar Plum'.

Plant:

*Type.*—Herbaceous perennial.

*Form.*—Clumping basal rosette.

*Hardiness.*—U.S.D.A. Hardiness Zones 5–9.

*Size.*—11 cm tall and 33 cm wide, not including inflorescence.

*Vigor.*—Excellent.

*Roots.*—With one main tap root, and many fibrous lateral branches, White 155A.

*Stem.*—Much congested, 1 cm deep and wide with no space between nodes.

Leaf:

*Type.*—Simple. Evergreen.

*Arrangement.*—Basal, with 12 to 24 leaves.

*Shape.*—Ovate.

*Blade size.*—Grows to 13.5 cm long and 9 cm wide.

*Venation.*—Pinnate.

*Margins.*—Strongly undulating. Irregularly crenate overall and toothed near base.

*Apex.*—Acute.

*Base.*—Obtuse.

*Surface texture.*—Leathery, rugose with stellate and velutinous hairs on both surfaces.

*Petiole.*—Size — 4.5 cm. long and grows to 0.9 cm wide. Surface texture — Stellate and velutinous hairs. Color — Yellow Green 145A to 145C with a pinker color up the middle, Greyed Purple 186C.

*Leaf color.*—Abaxial — Deep green. Closest to Green 147A with a prominent main vein, (Yellow Green 145A to 145C changing to a pinker color, Greyed Purple 186C, in the middle of the leaf). Adaxial — Yellow Green 147B.

Inflorescence:

*Type.*—Panicle.

*Number of panicles per plant in first flush.*—27.

*Cauline leaves.*—4 to 7 in number, crenate, sessile, ovate, 1.4 cm to 9 cm long and 1 to 5.5 cm wide. Cauline leaves have the same color, apex and base as basal leaves.

*Flower number.*—Count of 275 flowers on main panicle.

*Peduncle.*—Height — 29 cm to 39 cm. Diameter — 0.4 cm. near base. Surface texture — Glandular pubescent. Color — Yellow Green 146B.

*Pedicel.*—Length — 1.2 cm. Surface texture — Glandular pubescent. Color — Yellow Green 146C.

*Bloom time.*—June to August in Canby, Oreg.

Flower bud:

*Size.*—1.1 cm. wide and 0.8 cm. deep.

*Description.*—Pentagonal cushion.

*Surface.*—Glandular pubescent.

*Color.*—Violet 83A.

Flower:

*Type.*—Perfect. Complete. Irregular.

*Shape.*—Rotate, irregular, short tubular.

*Size.*—3.4 cm wide and 1.1 cm deep including stamens.

*Color.*—Violet 83B on both surfaces.

*Corolla.*—Petal description — 5 lobes, broadly obovate, margin entire, tip obtuse, base cuneate. Size — 3.4 cm wide and 0.4 cm deep. Surface — Backs glandular, inside glabrous.

*Calyx.*—Sepal description — Stellate, with 5 lobes, each lobe lanceolate with entire margins and an acuminate tip. Size — Grows to 1.2 cm. wide and 0.2 cm deep. Surface texture — Glandular pubescent on back, inside glabrous. Color — Yellow Green 147B on both surfaces.

*Stamens.*—Number — 5. Filaments — 0.7 cm. long, Yellow Orange 14A at base and heavily bearded Purple 77A on lower two stamens and Purple 77A topped with Yellow White 158C on upper three stamens. Anthers — Kidney shaped, 2 mm long. Greyed Purple 187A. Pollen — None.

*Pistil.*—Number — 1. Size — 1.2 cm long. Style — 1 cm long, Greyed Purple 187A. Stigma — Blunt, Yellow Green 146A. Ovary — Yellow Green 146A.

*Fragrance.*—None.

Fertility: Sterile, male and female. No pollen, fruit, or seed produced.

Disease and pests: None observed on plants grown commercially in Canby, Oreg. Powdery mildew and fungal leaf spot are possible. *Verbascum* are susceptible to caterpillars. No known resistance or susceptibility to disease.

COMPARISONS

This new cultivar is very similar in growth habit and flowering habit to *Verbascum* 'Jackie' (an unpatented plant). The greatest difference is the flower color. *V.* 'Jackie' is described as having copper colored buds that open to pale peach colored flowers and lavender stamens. The new cultivar *Verbascum* 'Sugar Plum' has purple buds, flowers and stamens and deeper green, undulating leaves.

I claim:

1. A new and distinct cultivar of *Verbascum* plant as herein illustrated and described.

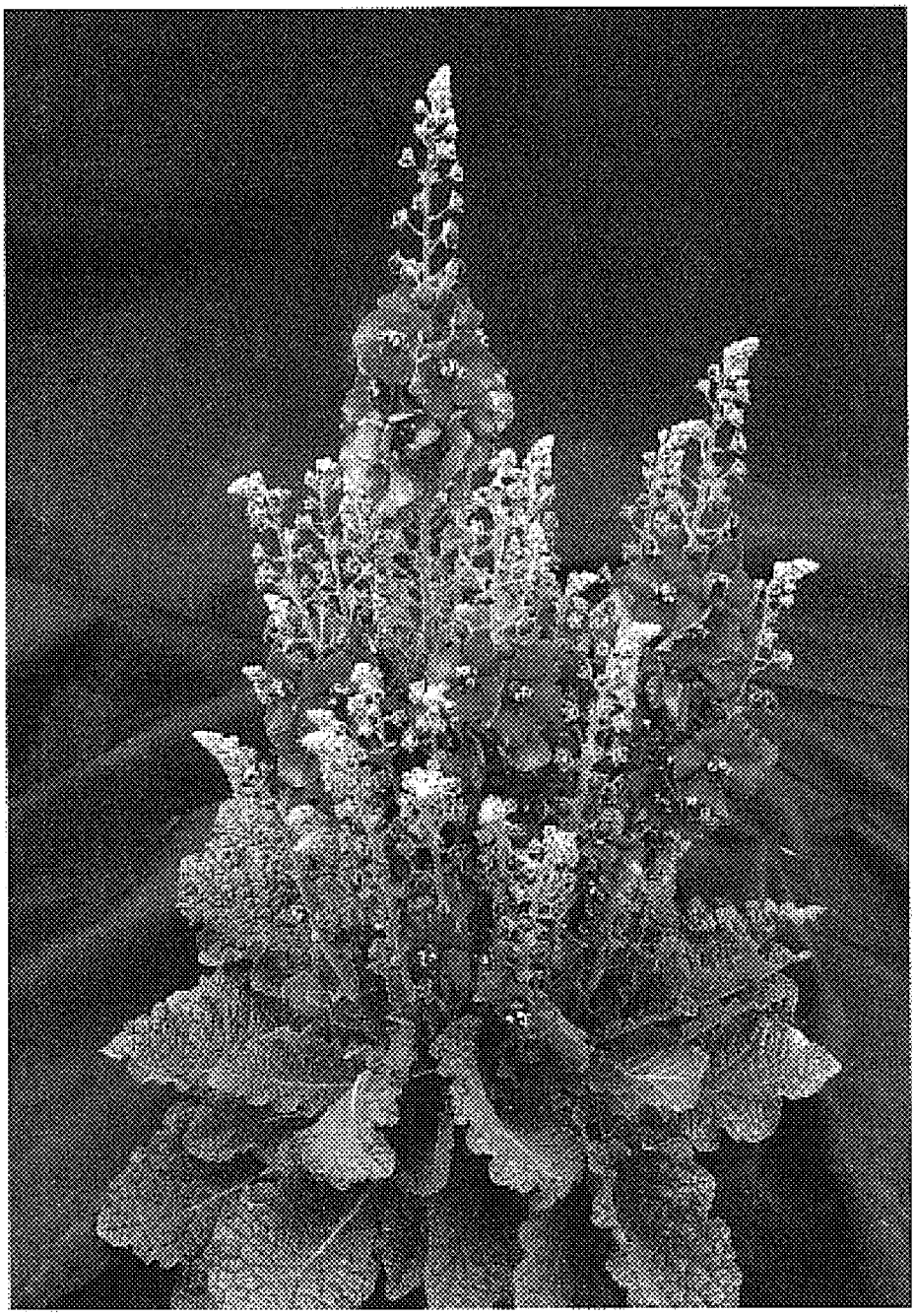

* * * * *